United States Patent [19]
Kawahara

[11] Patent Number: 6,028,911
[45] Date of Patent: Feb. 22, 2000

[54] X-RAY ANALYZING APPARATUS WITH ENHANCED RADIATION INTENSITY

[75] Inventor: Naoki Kawahara, Takatsuki, Japan

[73] Assignee: Rigaku Industrial Corporation, Osaka, Japan

[21] Appl. No.: 09/127,724

[22] Filed: Aug. 3, 1998

[51] Int. Cl.[7] .................................................. G01N 23/223
[52] U.S. Cl. ................................. 378/44; 378/45; 378/49
[58] Field of Search .......................................... 378/44–50

[56] References Cited

U.S. PATENT DOCUMENTS

| | | | |
|---|---|---|---|
| 5,220,591 | 6/1993 | Ohsugi et al. | 378/45 |
| 5,249,216 | 9/1993 | Ohsugi et al. | 378/46 |
| 5,408,512 | 4/1995 | Kuwabara et al. | 378/45 |

*Primary Examiner*—David P. Porta
*Attorney, Agent, or Firm*—Sughrue, Mion, Zinn, Macpeak & Seas, PLLC

[57] ABSTRACT

An X-ray analyzing apparatus includes a drive unit for moving a sample, a plurality of field-limiting slits each having a slit size corresponding to the size of a measuring area of the sample, a selector unit for selectively bringing the field-limiting slits into a path of travel of the secondary X-ray between the sample and the detecting unit, a drive controller for controlling the drive unit to move the sample according to the size of the measuring area of the sample to a position at which the intensity of radiation of a primary X-ray towards the measuring area of the sample attains a maximum value; and a selector controller for controlling the selector unit to render only the secondary X-ray emanating from the measuring area of the sample to be incident upon the detecting unit.

7 Claims, 6 Drawing Sheets

X-RAY ANALYZING APPARATUS WITH ENHANCED RADIATION INTENSITY

BACKGROUND OF THE INVENTION

1. Field of the Invention

The present invention relates to an X-ray analyzing apparatus for radiating a primary X-ray from an X-ray radiating source so as to irradiate a surface of a sample to be analyzed in a direction generally slantwise and for measuring the intensity of a secondary X-ray generated from the sample and, more particularly, to the X-ray analyzing apparatus capable of maximizing the utilization of the primary X-ray from the X-ray radiating source to accomplish the measurement with high precision.

2. Description of the Prior Art

A fluorescent X-ray analyzing apparatus has long been well known in the art, an example of which is shown in FIG. 10. The prior art fluorescent X-ray analyzing apparatus shown in FIG. 10 is so designed that a primary X-ray 3 generated from an X-ray radiating source 4 comprised of, for example, an X-ray tube is irradiated upon a sample 1 fixed on a sample support 2 and the intensity of a fluorescent X-ray 5 generated from the sample 1 can be measured by a detecting means 6. In this structure, the primary X-ray 3 is deemed to emit in a conical shape with respect to a center line (a principal radiating direction) represented by an axis T of the X-ray radiating source 4. In order to position the X-radiating source 4 so close to the sample that the sample 1 can be irradiated with an increased intensity of the primary X-ray 3 while assuming the fluorescent X-ray 5 generated from the sample 1 to be detected by the detecting means 6 without any interference with the X-ray radiating source 4, the principal radiating direction of the X-ray radiating source 4 is inclined at a predetermined angle, for example, 65°, relative to a surface 1a of the sample 1 confronting the X-ray radiating source 4 so that the sample 1 can be irradiated slantwise by the primary X-ray 3.

In this known fluorescent X-ray analyzing apparatus, a sample support 2 having the sample 1 fixed thereon is so positioned that the axis T of the X-ray radiating source 4 can reach and align with the center of a measuring area of the sample 1 (a measuring area N of the surface 1a of the sample 1 in the example shown in FIG. 10). In the illustrated example, the detecting means 6 includes a spectrometer or a monochromator 8, an X-ray detector 9, and a goniometer 18 for rotating the monochromator 8 and the detector 9 while the monochromator 8 and the detector 9 are kept in a predetermined relationship. The monochromator 8 and the detector 9 are drivingly associated with each other by means of the goniometer 18 so that respective angles of rotation of the monochromator 8 and the detector 9 with respect to an imaginary axis extending through the center of a surface 8a of the monochromator 8 at right angles to the plane of the drawing depicting FIG. 10 can assume a relationship of 1:2. With this construction, the intensity of the fluorescent X-ray 5 generated from the measuring area N of the sample 1 can be monochromated and measured for each wavelength. In other words, the prior art fluorescent X-ray analyzing apparatus employs an optical system of a so-called parallel beam method and is, in most cases, provided with a paralleling slit such as, for example, a solar slit, positioned between a field-limiting slit 19, as will be described later, and the monochromator 8 and between the monochromator 8 and the detector 9.

A slitted plate 20 is disposed between the sample 1 and the detecting means 6 and is formed with the field-limiting slit 19 having a slit size corresponding to the size of the measuring area N of the sample 1 and operable to pass therethrough only a fluorescent X-ray 5 generated from the measuring area N of the sample 1 while cutting off the fluorescent X-ray emanating from surroundings including the sample support 2. Although the fluorescent X-ray component 5 emits in all directions from the measuring area N of the sample 1, the slitted plate 20 and the detecting means 6 are so positioned that the amount of the fluorescent X-ray component 5 passing through the field-limiting slit 19 and subsequently incident upon the detecting means 6 can be maximized.

As discussed above, the sample 1 is so positioned that the axis T of the X-ray radiating source 4 can reach and align with the center of the measuring are an N of the sample 1. There is no specific reason for positioning the sample 1 in this way, but it is based on the fact that where the primary X-ray 3 from the X-ray radiating source 4 is to be irradiated towards the surface 1a of the sample 1 in a direction perpendicular thereto, the radiation can be maximized along the axis T of the X-ray radiating source 4.

When a simulation test was conducted to determine the pattern of distribution of radiation intensities of the primary X-ray 3 on an imaginary plane A to be radiated which includes the surface 1a of the sample 1 and a surface extension 1aa from the sample surface 1a, the inventor has found that where the primary X-ray 3 from the X-ray radiating source 4 was irradiated towards the sample surface 1a in a slantwise direction, as shown a curve B in FIG. 11, the radiation intensity distribution B did not attain a maximum value at a position C where the axis T of the X-ray radiating source 4 reaches the imaginary radiation plane A, but attained a maximum value at a peak position M displaced from the position C in a direction conforming to the direction of inclination of the X-ray radiating source 4, with the curve B consequently exhibiting an asymmetric distribution with respect to left and right sides. It has also been found that the reason therefor is because a left side of the position C on the imaginary radiation plane A is closer to the X-ray radiating source 4 than the position C on the same imaginary radiation plane A This result of the simulation test has been confirmed by a series of experiment conducted wherein an X-ray sensitive film was placed on the imaginary radiation plane A and exposed to the primary X-ray 3.

Accordingly, where, for example, a measuring area of the sample 1 is relatively small, say, having a diameter D5, that is, where the entirety of the surface 1a of the sample 1 which is small as shown in FIG. 10 is chosen to be the measuring area, or where although the sample 1 is not so small, only a small portion of the surface 1a of the sample 1 is chosen to be a measuring area, positioning of the sample 1 so that the axis T of the X-ray radiating source 4 can reach and align with the center of the measuring area such as hitherto practiced will result in utilization of an hatched area in FIG. 11 where the intensity of radiation of the primary X-ray 3 from the X-ray radiating source 4 is not maximum and, consequently, measurement with a sufficiently high accuracy cannot be accomplished. It is to be noted that numerical values depicted along the axis of abscissa in FIG. 11 are arbitrily chosen values to show relative relations and are not actual dimensions and, therefore, they have no unit.

SUMMARY OF THE INVENTION

Accordingly, the present invention has been devised with a view to substantially eliminating the above discussed problems inherent in the prior art fluorescent X-ray analyzing apparatus and is intended to provide an improved X-ray analyzing apparatus for radiating a primary X-ray from an X-ray radiating source so as to irradiate a surface of a sample in a direction generally slantwise and for measuring the intensity of a secondary X-ray generated from the sample and, more particularly, to the X-ray analyzing apparatus capable of maximizing the utilization of the primary X-ray from the X-ray radiating source to accomplish the measurement with high precision.

To this end, the present invention in accordance with one aspect thereof provides an X-ray analyzing apparatus which comprises a drive means for moving a sample, a plurality of field-limiting slits each having a slit size corresponding to the size of a measuring area of the sample, a selector means for selectively bringing the field-limiting slits into a path of travel of a secondary X-ray between the samples and a detecting means, a drive control means for controlling the drive means to move the sample according to the size of the measuring area of the sample to a position at which the intensity of radiation of a primary X-ray towards the measuring area of the sample attains a maximum value, and a selector control means for controlling the selector means to render only the secondary X-ray emanating from the measuring area of the sample to be incident upon the detecting means.

According to the above described construction, the sample can be moved according to the size of the measuring area of the sample to a position at which the intensity of radiation of a primary X-ray towards the measuring area of the sample attains a maximum value, and only the secondary X-ray emanating from the measuring area of the sample can be guided through the field-limiting slit so as to be incident upon the detecting means. Accordingly, utilization of the primary X-ray generated from the X-ray radiating source can be maximized to accomplish measurement with high accuracy.

In a preferred embodiment of the present invention, the drive control means is operable to control the drive means to move the sample according to the position of the measuring area of the sample to the position at which the intensity of radiation of the primary X-ray towards the measuring area of the sample attains the maximum value.

According to this preferred construction, since in accordance with the position of the measuring area of the sample the sample can be moved to the position at which the intensity of radiation of the p X-ray attains the maximum value, not only can utlization of the primary X-ray generated from the X-ray radiating source be maximized to accomplish measurement with high accuracy, but also measurement is possible with respect to the measuring area at an arbitrarily chosen position on the surface of the sample and, therefore, a so-called positional distribution analysis can be conducted.

The present invention according to another aspect provides an X-ray analyzing apparatus which comprises a plurality of field-limiting slits each having a slit size corresponding to the size of a measuring area of the sample, a selector means for selectively bringing the field-limiting slits into a path of travel of a secondary X-ray between a sample and a detecting means, a rotary support for rotating the sample, a drive control means for controlling the drive means to move the sample according to a position of the measuring area of the sample to an optimum position at which the intensity of radiation of a primary X-ray towards the measuring area of the sample is maximized, a rotation control means for controlling the rotary support so as to rotate the sample which has been moved to the peak position, and a selector control means for controlling the selector means to render only the secondary X-ray emanating from the measuring area of the sample to be incident upon the detecting means.

According to the above described construction, since the sample can be rotated about the optimum position, the intensity of radiation of the measuring area can be maximized and, also, averaged.

The drive means may be mounted on the rotary support if so desired.

Also, the X-ray analyzing apparatus of the above described construction may include a second rotary support supported by the drive means for rotating the sample.

In another preferred embodiment of the present invention, the drive means is preferably comprised of an X-Y stage capable of being moved in two directions in a plane parallel to the surface of the sample.

BRIEF DESCRIPTION OF THE DRAWINGS

In any event, the present invention will become more clearly understood from the following description of preferred embodiments thereof when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DETAILED DESCRIPTION OF THE EMBODIMENTS

Hereinafter, an X-ray analyzing apparatus according to a first preferred embodiment of the present invention will be discussed with reference to FIGS. 1 to 3.

Figure 1:
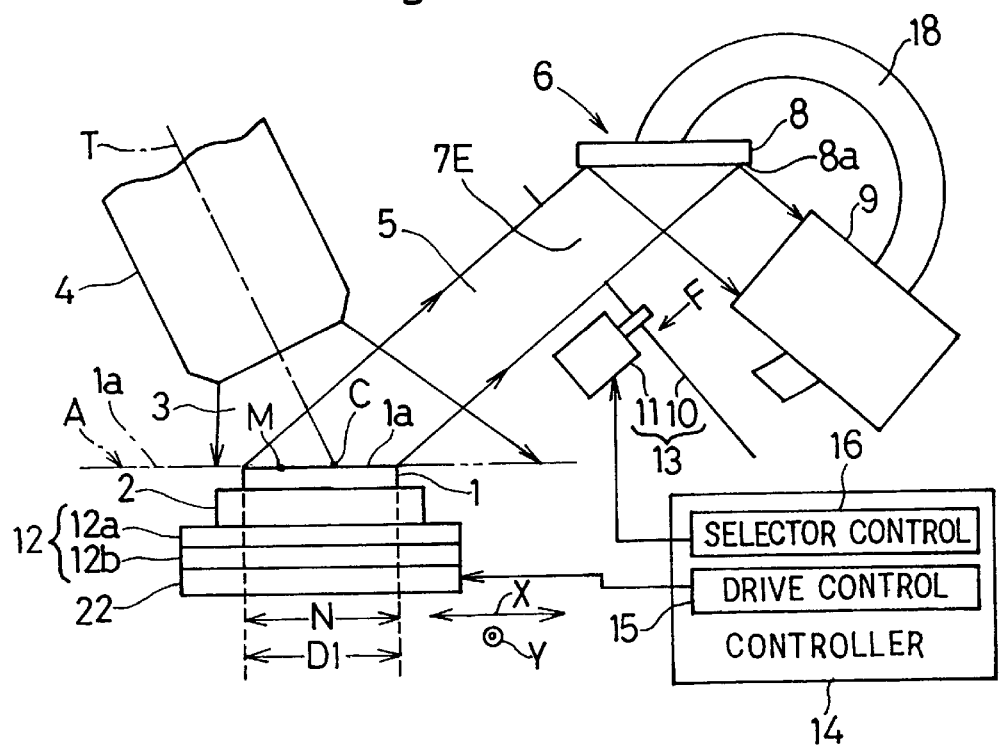
FIG. 1 is a schematic side view of an X-ray analyzing apparatus according to a first preferred embodiment of the present invention, showing a sample having a relatively large measuring area.

As shown in FIG. 1, the X-ray analyzing apparatus comprises a sample support 2 on which a sample 1 is fixedly placed, an X-ray radiating source 4 for radiating a primary X-ray 3 so as to impinge slantwise upon a surface 1a of the sample 1, and a detecting means 6 for measuring the intensity of a secondary X-ray 5 such as, for example, a fluorescent X-ray generated from the sample 1. The detecting means 6 includes an monochromator 8, a detector 9, and a goniometer 18 for rotating the monochromator 8 and the detector 9 while the monochromator 8 and the detector 9 are kept in a predetermined relationship. The sample support 2 is fixedly mounted on an upper member 12a of a two-dimensional drive means 12 positioned below the sample support 2. The drive means 12 is preferably employed in the form of, for example, an X-Y stage movable in X-axis and Y-axis directions perpendicular to each other in a plane below and parallel to the sample support 2. The X-Y stage forming the two-dimensional drive means 12 includes the upper member 12a, a lower member 12b and a base 22. The upper member 12a is movable in an X-axis direction, that is, leftwards and rightwards as viewed in the drawing depicting FIG. 1 relative to the lower member 12b, and the lower member 12b is positioned between the base 22 and the upper member 12a and movable in a Y-axis direction, that is in a direction perpendicular to the plane of the drawing depicting FIG. 1 relative to the base 22, said X-axis and Y-axis directions being perpendicular to each other. In other words, the X-axis and Y-axis directions conform respectively to the axes of abscissas and ordinates of the coordinate system on an imaginary radiation plane A including the surface 1a of the sample 1. It is also to be noted that the base 22 is adapted to be driven up and down by means of an elevating mechanism although the latter is not shown.

If desired, in place to the X-Y stage, the drive means 12 may comprise an rθ-stage, in which case rθ is defined on the imaginary radiation plane A and conforms to the polar coordinate system with the pole defined by the center point of the surface 1a of the sample 1.

The illustrated X-ray analyzing apparatus also comprises a substantially disc-shaped rotary slitted plate 10 having a plurality of, for example, five, field-limiting slits 7A, 7B, 7C, 7D and 7E of different slit sizes D1, D2, D3, D4 and D5 corresponding to respective sizes of measuring areas N of the samples 1, with the slit sizes D1 and D5 being the largest and the smallest of all. The plural field-limiting slits 7A to 7E are, as shown in FIG. 3 showing a plan view of the substantially disc-shaped rotary slitted plate 10 as viewed from the direction F in FIG. 1, formed in the substantially disc-shaped rotary slitted plate 10. The slitted plate 10 has a center portion 10c to which a drive shaft of a drive motor 11 is fixedly coupled so that when the slitted plate 10 is driven by the drive motor 11, the field-limiting slits 7A to 7E can be selectively brought into alignment with the path of travel of the fluorescent X-ray 5 between the sample 1 and the detecting means 6. The slitted plate 10 and the drive motor 11 altogether constitute a slit selector means 13.

The illustrated X-ray analyzing apparatus furthermore comprises a controller 14 which controls the entire apparatus on a basis of control programs installed. The controller 14 comprises a drive control means 15 for controlling the X-Y stage 12 to move the sample 1 according to the size of the measuring area N of and the position of the surface 1a of the sample 1 to a position at which the intensity of radiation of the primary X-ray 3 towards the measuring area N of the sample 1 attains a maximum value, and a selector control means 16 for controlling the drive motor 11 of the slit selector means 13 to select one of the field-limiting slits 7A to 7E so that only the secondary X-ray emanating from the measuring area N of the sample can be received by the detecting means 6. It is to be noted that the "intensity of radiation" of the primary X-ray 3 to the measuring area N of the sample 1 is intended to mean the sum of intensities of radiation of the primary X-ray 3 to the entirety of the measuring area N on the surface 1a of the sample 1.

Figure 2:
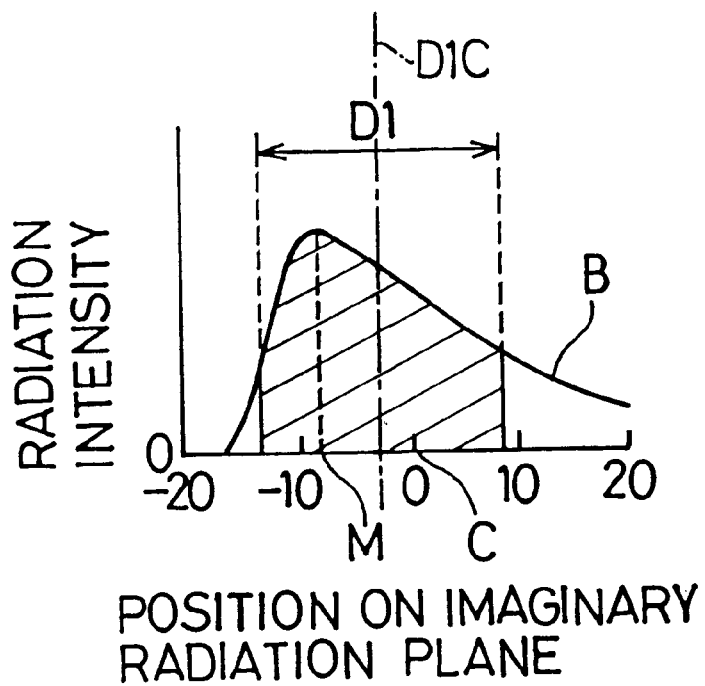
FIG. 2 is a graph showing a pattern of distribution of intensities of radiation of a primary X-ray on an imaginary irradiation plane, which is applicable where the primary X-ray is radiated slantwise, and also showing a position on the imaginary irradiation plane where the intensity of radiation of the primary X-ray on the large measuring area is maximized.
Figure 3:
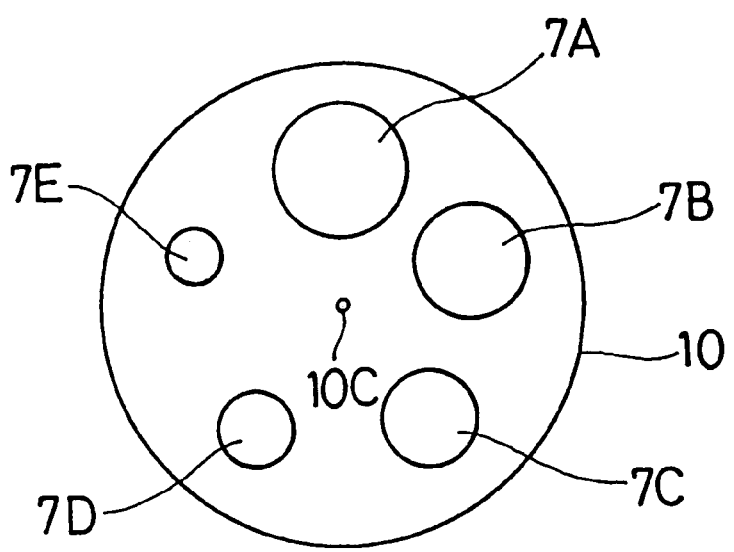
FIG. 3 is a schematic plan view of a slitted plate as viewed from a direction shown by F in FIG. 1.

In the meantime, as discussed hereinbefore, the pattern of distribution B of the intensities of radiation of the primary X-ray 3 on the imaginary irradiation plane A can be predefined as shown in FIG. 2 by means of a simulated calculation or an experiment in which the X-ray sensitive film is used. Once the pattern of distribution B of the intensities of radiation of the primary X-ray 3 has been predefined, and furthermore, calculation of areas enclosed by the distribution curve B within the diameter D of the measuring area N of the sample 1 are performed with measuring area N being shifted in a direction along the axis of abscissas, the maximum value of the surface area relative to the diameter D, that is, the maximum intensity of radiation can be determined. In this way, if determination is made to, for example, the case in which the measuring area N of the sample 1 has the maximum diameter D1 applied in this X-ray analyzing apparatus, the intensity of radiation of the primary X-ray 3 to the measuring area N of the sample 1 attains a maximum value within the hatched area shown in FIG. 2.

Figure 5:
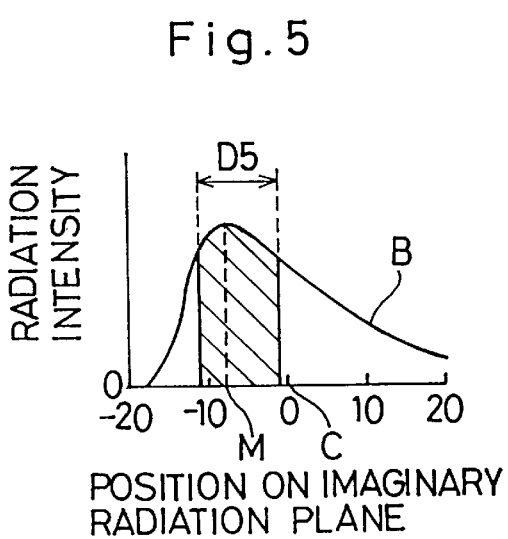
FIG. 5 is a graph showing a pattern of distribution of intensities of radiation of a primary X-ray on an imaginary irradiation plane, which is applicable where the primary X-ray is radiated slantwise, and also showing a position on the imaginary irradiation plane where the intensity of radiation of the primary X-ray on the large measuring area is maximized.

The position on the imaginary irradiation plane A shown in FIG. 1 which corresponds to the hatched area, that is, the position at which the maximum intensity of radiation is attained is stored in the drive control means 15 as a position corresponding to the diameter D1 of the measuring area N with a position C taken as reference at which an axis T of the X-ray radiating source 4 reaches the imaginary irradiation plane A. Similarly, respective positions representative of the maximum intensities of radiation corresponding to the diameters D2, D3, D4 and D5 of other measuring areas are stored in the drive control means 15. As another example, the position at which the intensity of radiation of the primary X-ray 3 to the measuring area N is maximized at the position corresponding to the smallest diameter D5 of the measuring area N applicable in the X-ray analyzing apparatus is shown in FIG. 5. It is to be noted that the pattern of distribution B of radiation of the primary X-ray 3 on the imaginary irradiation plane A shown in FIGS. 2 and 5 are only for the purpose of illustration and may vary depending on characteristics of the X-ray radiating source 4 and the position thereof relative to the imaginary irradiation plane A.

On the other hand, once the size and the position of the measuring area N of the sample 1 have been fixed, the size and the position of one of the field-limiting slits 7 required to render only the fluorescent X-ray 5, generated from the measuring area N, to be incident upon the detecting means 6 are also fixed. Based on this, the diameter of each of the field-limiting slits 7A, 7B, 7C, 7D and 7E and the distance from the center portion 10c of the slitted plate 10 shown in FIG. 3 are predefined. Simultaneously therewith, correspondence of the diameters D1, D2, D3, D4 and D5 of the measuring area N with the respective field-limiting slits 7A, 7B, 7C, 7D and 7E is stored in the selector control means 16. In addition, the X-ray analyzing apparatus embodying the present invention may have a paralleling slit positioned between the field-limiting slits 7 and the monochromator 8 and also between the monochromator 8 and the detector 9 as is the case with the prior art X-ray analyzing apparatus.

It is to be noted that where a semiconductor detector of a high energy resolving power is used for the detector 9, the detecting means 6 may not be provided with the monochromator 8 and the goniometer 18. It is also to be noted that an optical system of the parallel beam method may not be necessarily employed, but an optical system of a focusing method may be employed. Where the optical system of the focusing method is employed, a curvity crystal is employed as an monochromator and the detector is to be positioned at the point of focus and no paralleling slit is employed.

The operation of the X-ray analyzing apparatus of the structure described above will now be described. In the first place, the case will be discussed in which the entire surface 1a of the sample 1 or a central portion of the surface 1a of the sample 1 is chosen as a measuring area N. Assuming that an analyzing program installed in the controller 14 is selected and executed, the sample 1 is to be fixed with its center aligned with the center of the sample support 2. Then, as shown in FIG. 1, where the measuring area N of the sample 1 has, for example, a size corresponding to the largest diameter D1 applicable in the X-ray analyzing apparatus, correspondence of the size of the measuring area N with the largest diameter D1 is inputted to both of the control means 15 and 16 by means of the analyzing program. The drive control means 15 then controls the X-Y stage 12 so that the sample support 2 can be moved to the position corresponding to the diameter D1 of the measuring area N stored therein, that is, the position at which the intensity of radiation of the primary X-ray 3 to the measuring area N of the sample 1 can be maximized. Simultaneously therewith, the selector control means 16 controls the drive motor 11 to rotate the slitted plate 10 to select the field-limiting slit 7A corresponding to the diameter D1 of the measuring area N of the sample 1, thereby bringing the field-limiting slit 7A into alignment with the path of travel of the fluorescent X-ray 5 between the sample 1 and the detecting means 6. In this way, the condition shown in FIG. 1 is established.

Figure 4:
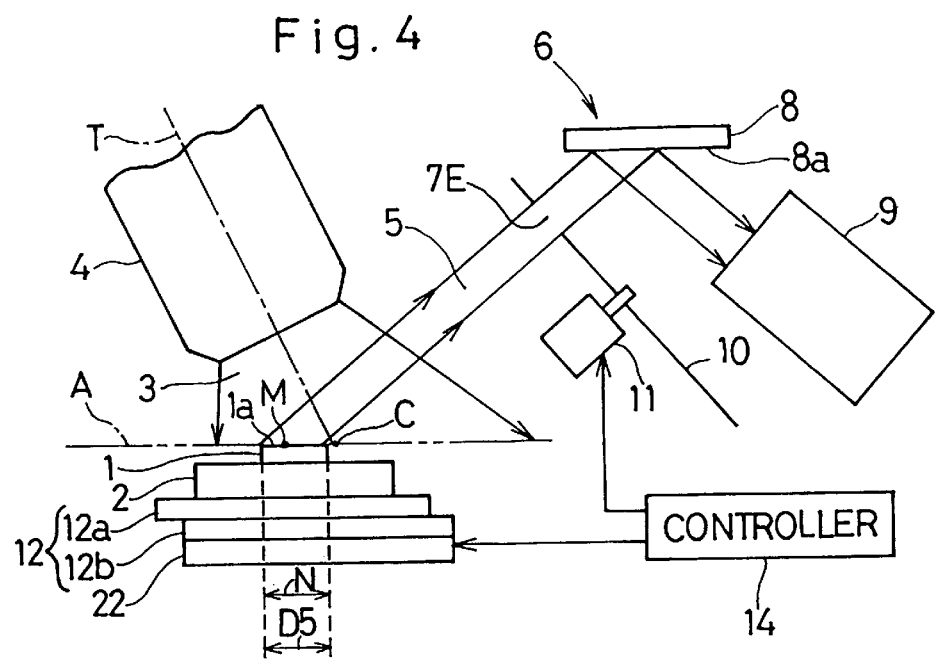
FIG. 4 is a schematic side view of the X-ray analyzing apparatus according to a first preferred embodiment of the present invention, showing the sample having a relatively small measuring area.

On the other hand, where the measuring area N of the sample 1 has, for example, a size corresponding to the smallest diameter D5 applicable in the X-ray analyzing apparatus as shown in FIG. 4, correspondence of the size of the measuring area N of the sample 1 with the diameter D5 is inputted to both of the control means 15 and 16, and the drive control means 15 then controls the X-Y stage 12 so that the sample support 2 can be moved to the position corresponding to the diameter D5 of the measuring area N stored therein, that is, the position at which the intensity of radiation of the primary X-ray 3 to the measuring area N of the sample 1 can be maximized. Simultaneously therewith, the selector control means 16 controls the drive motor 11 to rotate the slitted plate 10 to select the field-limiting slit 7E corresponding to the diameter D5 of the measuring area N of the sample 1, thereby bringing the field-limiting slit 7E into alignment with the path of travel of the fluorescent X-ray 5 between the sample 1 and the detecting means 6. In this way, the condition shown in FIG. 4 is established At this time, the incident area the fluorescent X-ray 5, emanating from the measuring area N of the diameter D5 on the detecting means 6, or the incident area on the surface 8a of the monochromator 8 and the incident area on a surface of the detector 9 so far shown in FIG. 4, may vary as compared with those when the measuring area N is of a size corresponding to the diameter D1, but it can be encompassed within the incident area on the surface 8a of the monochromator 8 in the case of the diameter D1 which is the largest diameter and, therefore, no problem occurs. Even where the measuring area N is of a size corresponding to any one of the diameters D2, D3 and D4, a control similar to that described above takes place.

Thus, with the X-ray analyzing apparatus embodying the present invention, according to the size of the measuring area N of the sample 1, the sample support 2 can be moved to the position at which the intensity of radiation of the primary X-ray 3 to the measuring area N of the sample 1 can be maximized and only the fluorescent X-ray emanating from the measuring area N of the sample 1 is made incident upon the detecting means 6. Accordingly, utilization of the primary X-ray 3 generated from the X-ray radiating source 4 can be minimized to accomplish measurement with a sufficiently high accuracy.

Figure 6:
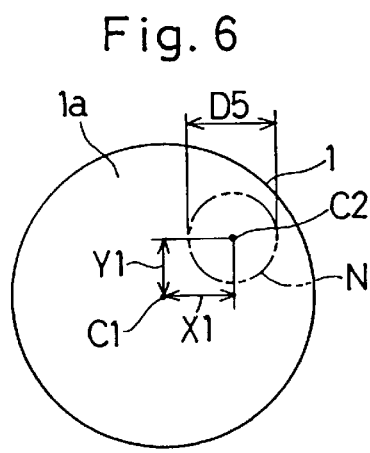
FIG. 6 is a schematic plan view showing the sample.

The operation of the X-ray analyzing apparatus which takes place when an area of the surface 1a of the sample 1 other than the center portion is taken as a measuring area N will now be described. In the first place, assuming that an analyzing program installed in the controller 14 is selected and executed, the sample 1 is to be fixed with its center aligned with the center of the sample support 2. Then, as shown in FIG. 6, where the measuring area N of the sample 1 has, for example, a size corresponding to the smallest diameter D5 applicable in the X-ray analyzing apparatus and a center C2 of the measuring area N is positioned at a location (x1, y1) of the X-Y coordinate system on the imaginary irradiation plane A with its origin occupied by a center C1 of the surface 1a of the sample 1, such correspondence is inputted to both of the control means 15 and 16. Then, the drive control means 15 controls the X-Y stage 12 so that the sample support 2 is moved to a position offset (−x1, −y1) from the position corresponding to the diameter D5 of the measuring area N stored, that is, the position at which the intensity of radiation of the primary X-ray 3 to the measuring area N of the sample 1 can be maximized. Simultaneously therewith, the selector control means 16 controls the drive motor 11 to rotate the slitted plate 10 to select the field-limiting slit 7E corresponding to the diameter D5 of the measuring area N of the sample 1, that is, so as to allow only the fluorescent X-ray 5, emanating from the measuring area N of the sample 1, to be incident upon the detecting means 6, and the drive motor 11 is consequently driven to bring the field-limiting slit 7E into alignment with the path of travel of the fluorescent X-ray 5 between the sample 1 and the detecting means 6.

As hereinbefore described, with the X-ray analyzing apparatus embodying the present invention, since the sample support 2 can be moved to the position at which the intensity of radiation of the primary X-ray 3 to the measuring area N of the sample 1 can be maximized, according to not only the size of the measuring area N of the sample 1, but also the position of the measuring area N on the surface 1a of the sample 1, the primary X-ray 3 from the X-ray radiating source 4 can be sufficiently utilized at the measuring area N at any arbitrarily chosen position on the surface 1a of the sample 1 to accomplish the measurement with a high accuracy. Also, by continuously or intermittently moving the measuring area N on the surface 1a of the sample 1, a so-called positional distribution analysis of elements contained in the sample 1 can also be performed while maintaining effects similar to those described above.

Figure 10:
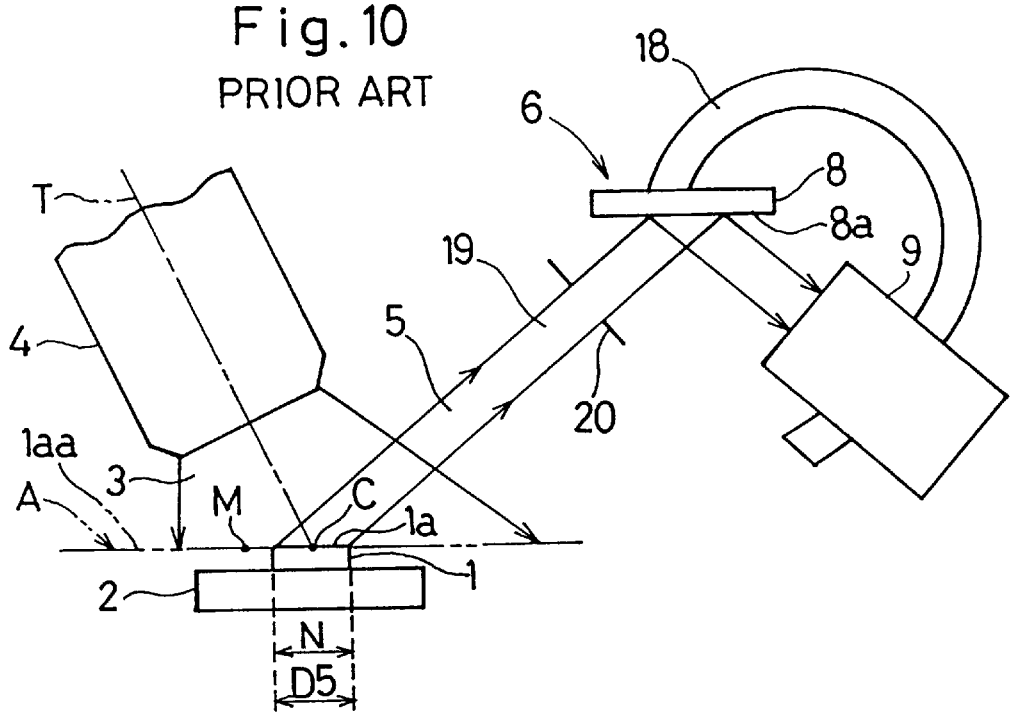
FIG. 10 is a schematic side view showing the prior art X-ray analyzing apparatus.
Figure 11:
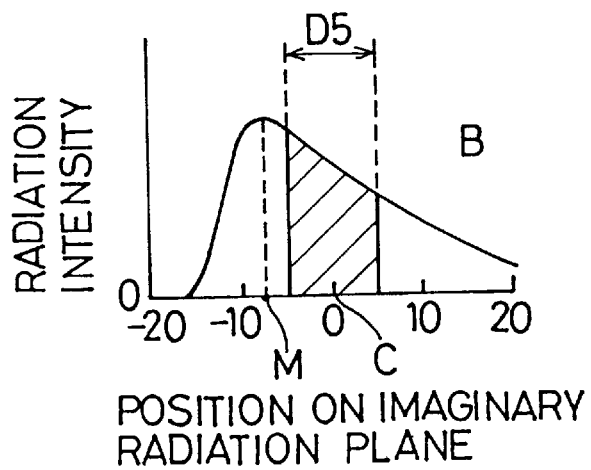
FIG. 11 is a graph showing a pattern of distribution of intensities of radiation of a primary X-ray on an imaginary irradiation plane, which is applicable where the primary X-ray is radiated slantwise in the prior art X-ray analyzing apparatus, and also showing a position of irradiation of the primary X-ray on a small measuring area on the imaginary irradiation plane.

In contrast thereto, where the positional distribution analysis is to be carried out with the use of the prior art technique shown in FIG. 10 and wherein the detecting means 6 is moved relative to the fixed X-ray radiating source 4 and the fixed sample 1, the intensity of radiation of the primary X-ray 3 may vary depending on the measuring area and, therefore, the result of measurement will require compensation. Also, where the positional distribution analysis is to be carried out with the use of the prior art technique wherein the sample 1 is moved relative to the fixed X-ray radiating source 4 and the fixed detecting means 6, although no compensation is required because the intensity of radiation of the primary X-ray 3 remains constant regardless of change of the measuring area, such constant intensity of radiation of the X-ray 3 is attributable to the condition in which the position C at which the axis T of the X-ray radiating source 4 reaches is aligned with the center C2 of the measuring area N and, therefore, a problem remains unsolved in which the primary X-ray 3 from the X-ray radiating source 4 cannot be sufficiently highly utilized and, therefore, no measurement can be accomplished with a high accuracy.

Figure 7:
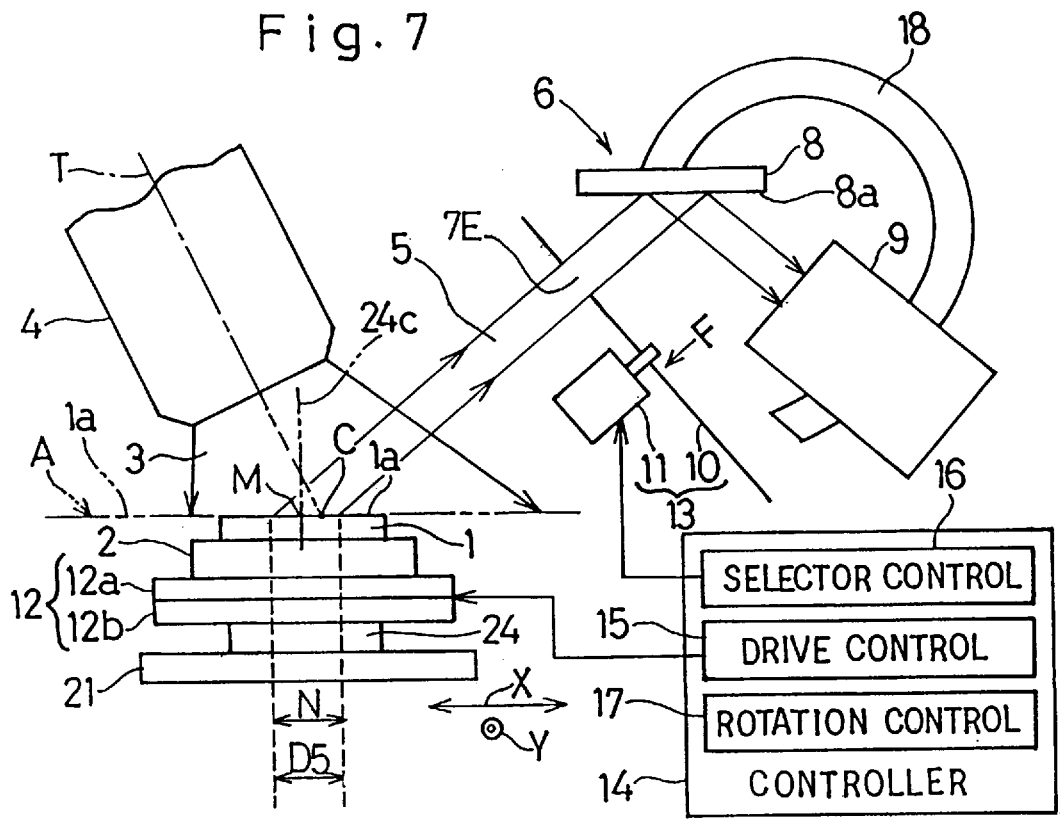
FIG. 7 is a schematic side view of the X-ray analyzing apparatus according to a second preferred embodiment of the present invention.
Figure 8:
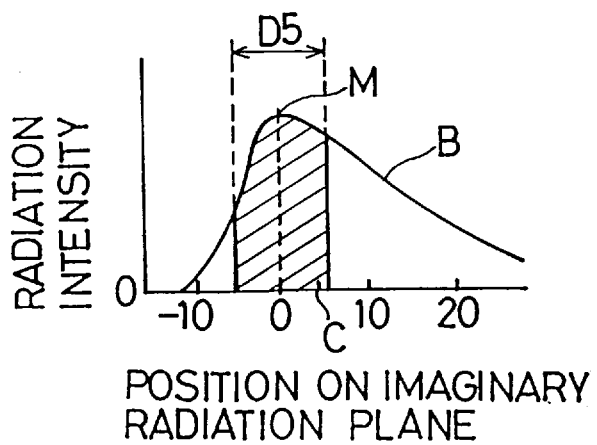
FIG. 8 is a graph showing a pattern of distribution of intensities of radiation of the primary X-ray on an imaginary irradiation plane.

FIG. 7 illustrates the X-ray analyzing apparatus according to a second preferred embodiment of the present invention. Referring now to FIG. 7, the first drive means 12 comprising the X-Y stage for the support of the sample support 2 thereon is mounted on a rotary support 24, such as a rotary table. The rotary table 24 is in turn mounted on the base 21 and is rotatable about a table center 24c lying perpendicular to the surface 1a of the sample 1 to rotate the first X-Y stage 12 about the table center 24c. This table center 24c is aligned with a peak position M (one of the optimum positions) at which the pattern of distribution B of the intensities of radiation shown in FIG. 8 on the imaginary irradiation plane A containing the surface 1a of the sample 1 is maximized. In FIG. 8, only the pattern of distribution B of the intensities of radiation associated with the measuring area N having a relatively small diameter D5 is shown. This peak position M is fixed for a particular X-ray analyzing apparatus and will not vary regardless of change in intensity of radiation. Other mechanical structures are substantially similar to those of the X-ray analyzing apparatus according to the previously described first embodiment of the present invention.

However, the controller 14 employed in the X-ray analyzing apparatus shown in FIG. 7 includes a drive control means 15A for controlling the X-Y stage 12 so as to move the center of the measuring area N of the sample 1, which has been offset from a center portion of the sample 1, to the previously described peak position M, a selector control means 16 for selecting one of the field-limiting slits 7A to 7E according to the size of the measuring area N of the sample 1, and a rotation control means 17, all built therein. The rotation control means 17 is operable to cause the rotary table 24 to undergo one or more complete rotation, that is, a 360° or more rotation, after the drive control means 15A has caused the X-Y stage 12 to move the sample support 2 to a position where the center of the measuring area N is brought into alignment with the peak position M. The measuring area N may be a center portion of the sample 1 or a portion offset from the center portion of the sample 1 and, therefore, it is possible to accomplishing a mapping measurement in which the measurement can be carried out at a plurality of measuring areas N of the sample 1.

As hereinabove described, since the sample 1 undergoes an angular movement about the peak position M, an area in which the pattern of distribution B of the intensities of radiation is maximum can be averaged and utilized, particularly when the measuring area N of the sample 1 is of a relatively small size and, therefore, the intensity of radiation is maximum at the measuring area N of the sample 1 and averaged.

Where the measuring area N of the sample 1 is small such as in the embodiment of the present invention as shown in FIG. 7, utilization of an area adjacent the peak position M at which the distribution of the radiation intensities of radiation is large is effective to maximize the intensity of radiation of the measuring area N. In other words, this peak position M will be the optimum position. However, where the measuring area N is large, it may occur that by the reason discussed in connection with and with reference to FIG. 2, the optimum position at which the intensity of radiation of this measuring area N will become high may offset from the peak position M. By way of example, if the measuring area N has a large diameter D1, the optimum position at which the intensity of radiation of this measuring area N attains the highest value, that is, the optimum position of the center of D1 will be the position indicated by D1C.

Figure 9:
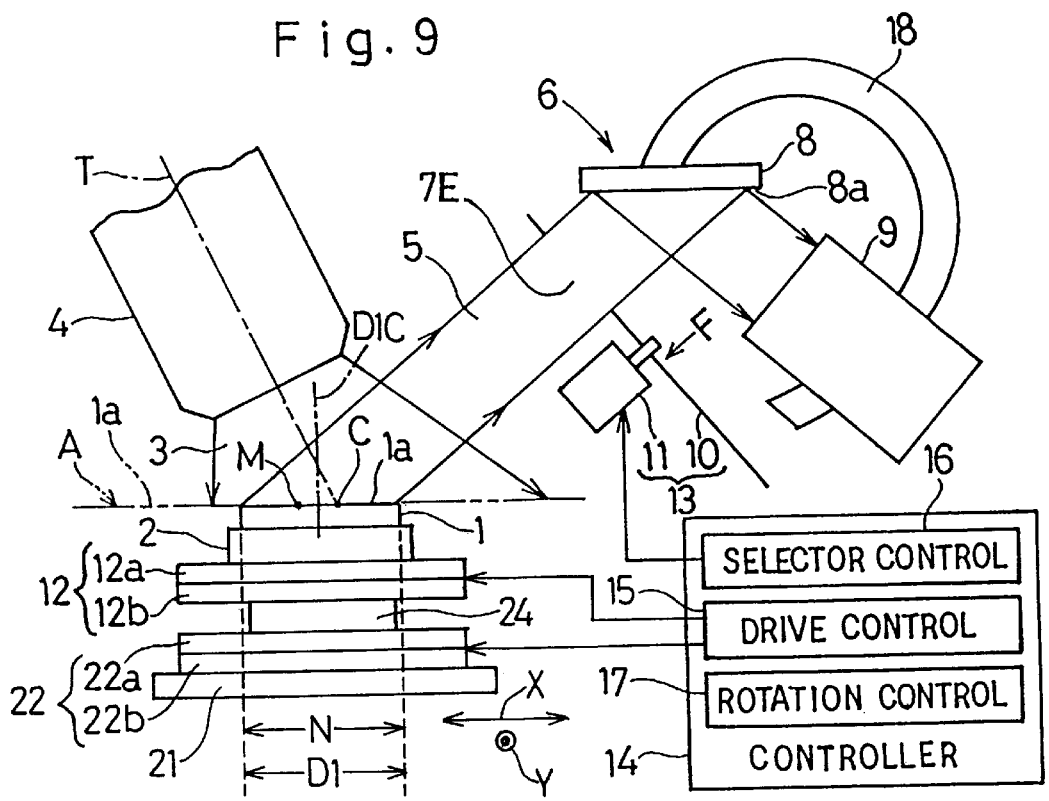
FIG. 9 is a schematic side view showing the X-ray analyzing apparatus according to a third preferred embodiment of the present invention.

In view of the above, in the third preferred embodiment of the present invention shown in FIG. 9, a second drive means 22 comprising an X-Y stage for the support of the rotary table 24 is mounted on the base 21. This second drive means 22 may be in the form of an X stage or a Y stage capable of undergoing a linear movement in one direction. The sample 1 can be, as is the case with that shown in FIG. 7, supported on the first drive means 21 through the sample support 2, which first drive means 12 is in turn mounted on the rotary table 24.

According to the embodiment shown in FIG. 9, the sample 1 can be moved by the second X-Y stage 22 to the optimum position at which the maximum intensity of radiation can be obtained, that is, the position at which the center of the measuring area N aligns with the previously discussed position D1C (shown in FIG. 2). In this condition, the fluorescent X-ray measurement is carried out while the second rotary support 24 is rotated to rotate the sample about the position D1C. In this way, the intensity of radiation of the measuring area N becomes large and averaged. Also, where the measuring area N is a portion offset from the center of the sample , the sample 1 can be moved by the first X-Y stage 12 until the center of the measuring area N can be aligned with the position D1C and, thereafter, by rotating the first rotary support 24 while the center of the measuring area N is aligned with the position D1C, to perform the fluorescent X-ray measurement. Thus, it is possible to accomplish the mapping measurement in which the measurement is carried out with the plural measuring areas N of the sample 1.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

What is claimed is:

1. An X-ray analyzing apparatus which comprises:

a source of X-ray for irradiating a surface of a sample in a slantwise direction;

a detecting means for measuring an intensity of a secondary X-ray generated from the sample;

a drive means for moving the sample;

a plurality of field-limiting slits each having a slit size corresponding to the size of a measuring area of the sample;

a selector means for selectively bringing the field-limiting slits into a path of travel of the secondary X-ray between the sample and the detecting means one at a time;

a drive control means for controlling the drive means to move the sample according to the size of the measuring area of the sample to a position at which the intensity of radiation of a primary X-ray towards the measuring area of the sample attains a maximum value; and a selector control means for controlling the selector means to render only the secondary X-ray emanating from the measuring area of the sample to be incident upon the detecting means.

2. The X-ray analyzing apparatus as claimed in claim 1, wherein the drive control means controls the drive means to move the sample according to the position of the measuring area of the sample to the position at which the intensity of radiation of the primary X-ray towards the measuring area of the sample attains the maximum value.

3. The X-ray analyzing apparatus as claimed in claim 1, wherein the drive means comprises an X-Y stage movable in two dimensional directions in a plane parallel to the surface of the sample.

4. An X-ray analyzing apparatus which comprises:

a source of X-ray for irradiating a surface of a sample in a slantwise direction;

a detecting means for measuring an intensity of a secondary X-ray generated from the sample;

a drive means for moving the sample;

a plurality of field-limiting slits each having a slit size corresponding to the size of a measuring area of the sample;

a selector means for selectively bringing the field-limiting slits into a path of travel of the secondary X-ray between the sample and the detecting means one at a time;

a drive control means for controlling the drive means to move the sample according to a position of the measuring area of the sample to an optimum position at which the intensity of radiation of a primary X-ray towards the measuring area of the sample is maximized;

a rotary support for rotating the sample by rotating the drive means;

a rotation control means for controlling the rotary support so as to rotate the sample which has been moved to the optimum position; and a selector control means for controlling the selector means to render only the secondary X-ray emanating from the measuring area of the sample to be incident upon the detecting means.

5. The X-ray analyzing apparatus as claimed in claim 4, wherein the drive means is supported on the rotary support.

6. The X-ray analyzing apparatus as claimed in claim 4, further comprising an additional rotary support for rotating the sample, said additional rotary support being supported by the drive means.

7. The X-ray analyzing apparatus as claimed in claim 4, wherein the drive means comprises an X-Y stage movable in two dimensional directions in a plane parallel to the surface of the sample.

* * * * *